United States Patent
Ueno et al.

(10) Patent No.: US 7,262,304 B2
(45) Date of Patent: Aug. 28, 2007

(54) ONE-POT PROCESS FOR THE PREPARATION OF 1,2-BENZISOXAZOLE-3-METHANESULFONAMIDE

(75) Inventors: Yoshikazu Ueno, Osaka (JP); Tsutomu Ishikura, Naka (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 11/447,099

(22) Filed: Jun. 6, 2006

(65) Prior Publication Data

US 2006/0229454 A1    Oct. 12, 2006

Related U.S. Application Data

(63) Continuation of application No. 11/088,802, filed on Mar. 25, 2005, now Pat. No. 7,081,539.

(60) Provisional application No. 60/556,073, filed on Mar. 25, 2004.

(51) Int. Cl.
    C07D 261/20    (2006.01)

(52) U.S. Cl. .................................... 548/241

(58) Field of Classification Search ................. 548/241
    See application file for complete search history.

(56) References Cited

U.S. PATENT DOCUMENTS

| | | | |
|---|---|---|---|
| 3,145,082 A | 8/1964 | Rausch et al. | |
| 4,172,896 A | 10/1979 | Uno et al. | |
| 6,677,458 B2 * | 1/2004 | Mendelovici et al. | 548/241 |
| 6,841,683 B2 | 1/2005 | Mendelovici et al. | |
| 2002/0183525 A1 | 12/2002 | Mendelovici et al. | |
| 2003/0114682 A1 | 6/2003 | Nidam et al. | |
| 2003/0144527 A1 | 7/2003 | Nidam et al. | |
| 2004/0014983 A1 | 1/2004 | Mendelovici et al. | |
| 2004/0049053 A1 | 3/2004 | Mendelovici et al. | |
| 2004/0242931 A1 | 12/2004 | Williams | |

FOREIGN PATENT DOCUMENTS

| | | |
|---|---|---|
| JP | 53-77057 | 7/1978 |
| JP | 54-163570 | 12/1979 |
| JP | 54-163823 | 12/1979 |
| WO | 03-031330 A1 | 4/2003 |
| WO | 2005/044808 | 5/2005 |

OTHER PUBLICATIONS

Hitoshi Uno et al., "Studies on 3-Substituted 1,2-Benzisoxazole Derivatives. 6. Syntheses of 3-(Sulfamoylmethyl)-1,2-benzisoxazole Derivatives and Their Anticonvulsant Activities", J. Med. Chem., 22, pp. 180-183, 1979.
A. Mustafa et al., "Experiments With Substituted (3,2-c)-Pyranyl-2,10-Diones and Benzopyranyl-(3,2-c) Pyran-2,8-Diones", Tetrahedron, 19, pp. 1831-1839, 1963.
Giovanni Casini et al., "On 1,2-Benzisoxazole-3-acetic Acid and 3-Methyl-1,2-benzisoxazole: a Restatement", J. Heterocycl. Chem., 6, pp. 279-283, 1969.
Mario Giannella et al., "Benzisoxazole and Benzisothiazole Analogs of Auxin", Phytochemistry, 10, pp. 539-544, 1971.
P. Thourel et al., Syntheses D'Acide Benzisoxazole-1,2 Acetique-3 ($^{14}$C-α) ET($^{14}$C-β), J. Labell. Compd. Radiopharm., 25, pp. 1235-1244, 1988.
Masanao Shimizu et al., "Research and Development of Zonisamide, a New Type of Antiepileptic Drug", Yakugaku-Zasshi, vol. 116, pp. 533-547, 1996.
Hitoshi Uno et al., "Studies on 3-Substituted 1,2-Benzisoxazole Derivatives. V. [1)] Electrophilic Substitutions of 1,2-Benzisoxazole-3-acetic Acid", Chem. Pharm. Bull, 26, 11, pp. 3498-3503, 1978.
Giovanni Casini et al., "On 1,2-Benzisoxazole-3-acetic Acid (1)", J. Heterocycl. Chem., 2, 385-386, 1965.

* cited by examiner

*Primary Examiner*—Kamal A. Saeed
(74) *Attorney, Agent, or Firm*—Fitch Even Tabin & Flannery

(57) ABSTRACT

A process for the preparation of 1,2-benzisoxazole-3-methanesulfonamide without isolation of intermediates in solid form, by using 4-hydroxycoumarin as a starting compound, and water and 1,2-dichloroethane as solvents; and an industrially useful process for the preparation of 1,2-benzisoxazole-3-acetic acid, by reacting 4-hydroxycoumarin and hydroxylamine in water.

5 Claims, No Drawings

=== PAGE 1 ===

ONE-POT PROCESS FOR THE PREPARATION OF 1,2-BENZISOXAZOLE-3-METHANESULFONAMIDE

CROSS REFERENCE

This application is a continuation of U.S. application Ser. No. 11/088,802, filed Mar. 25, 2005, now U.S. Pat. No. 7,081,539 B2, which is based on U.S. provisional Application No. 60/556,073, filed Mar. 25, 2004.

TECHNICAL FIELD

The present invention relates to a process for the preparation of 1,2-benzisoxazole-3-methanesulfonamide being useful as an antiepileptic agent from 4-hydroxycoumarin as a starting compound without isolating intermediates in solid form.

BACKGROUND ART

JP-A-53-77057 discloses a process for the preparation of 1,2-benzisoxazole-3-methanesulfonamide from 1,2-benzisoxazole-3-acetic acid as a starting compound. In this process, the intermediate, sodium 1,2-benzisoxazole-3-methanesulfonate, is isolated in solid form from a water layer, and there is a removal operation of insoluble material from a reaction mixture. Processes for the preparation of 1,2-benzisoxazole-3-methanesulfonamide comprising a reaction of isolated sodium 1,2-benzisoxazole-3-methanesulfonate in solid form are disclosed in U.S. Pat. No. 4,172,896, JP-A-54-163823 and Uno, et al., J. Med. Chem., 22,180 (1979). A. Mustafa et al., Tetrahedron, 19, 1831 (1963), G. Casini, et al., J. Heterocycl. Chem., 6, 279 (1969), M. Giannella, et. al., Phytochemistry, 10, 539 (1971), P. Thourel, et al., J. Labell. Compd. Radiopharm., 25, 1235 (1988), US 2002/0183525 A1 and US 2004/0049053 A1 disclose a process for the preparation of 1,2-benzisoxazole-3-acetic acid or its derivatives from 4-hydroxycoumarin or its derivatives. However, these literatures disclose neither a reaction using only water as a solvent nor a reaction involving a chelating agent. US 2003/0114682 A1 and US 2003/0144527 A1 disclose a process for the preparation of sodium 1,2-benzisoxazole-3-methanesulfonate from 1,2-benzisoxazole-3-acetic acid. US 2004/0014983 A1 discloses processes for the preparation of 1,2-benzisoxazole-3-methanesulfonyl chloride from sodium 1,2-benzisoxazole-3-methanesulfonate, and 1,2-benzisoxazole-3-methanesulfonamide from 1,2-benzisoxazole-3-methanesulfonyl chloride. In M. Shimizu, et al., Yakugaku-Zasshi, vol. 116, p. 533-547 (1996), an industrial process for the preparation of 1,2-benzisoxazole-3-methanesulfonamide via 1,2-benzisoxazole-3-acetic acid, sodium 1,2-benzisoxazole-3-methanesulfonate and 1,2-benzisoxazole-3-methanesulfonyl chloride as an intermediate is disclosed using 4-hydroxycoumarin as a starting compound. However, these literatures do not disclose a one-pot process for the preparation of 1,2-benzisoxazole-3-methanesulfonamide using 4-hydroxycoumarin or 1,2-benzisoxazole-3-acetic acid as a starting compound without isolating intermediates in solid form.

SUMMARY OF INVENTION

The present inventors have intensively studied an industrially efficient process for the preparation of 1,2-benzisoxazole-3-methanesulfonamide, which is economically excellent and is capable of efficient operations, and have found that when 1,2-dichloroethane is used as a solvent, 1,2-benzisoxazole-3-methanesulfonamide can be synthesized from 1,2-benzisoxazole-3-acetic acid as a starting compound without isolating intermediates (e.g., sodium 1,2-benzisoxazole-3-methanesulfonate, etc.) in solid form in each step, and when water and 1,2-dichloroethane are used as a solvent, 1,2-benzisoxazole-3-methanesulfonamide can be synthesized from 4-hydroxycoumarin as a starting compound without isolating intermediates in solid form in each step, and they have accomplished the present invention. Moreover, the present inventors also have intensively studied a process for the preparation of 1,2-benzisoxazole-3-acetic acid, which is a first step of the present process, and have found a process wherein the desired 1,2-benzisoxazole-3-acetic acid can be obtained in high yield by reacting 4-hydroxycoumarin and hydroxylamine using only water as a solvent, and further have found that a rapid decomposition of hydroxylamine, which may unexpectedly occur otherwise, can be suppressed when this reaction is carried out in the presence of a chelating agent, by which the reaction temperature can be easily controlled, making the present process even more desirable.

DETAILED DESCRIPTION OF INVENTION

The present invention provides a process for the preparation of 1,2-benzisoxazole-3-methanesulfonamide, which comprises:

(a) reacting 4-hydroxycoumarin, hydroxylamine or an acid addition salt thereof, and a base in water to give a first mixture;

(b) acidifying the first mixture, adding 1,2-dichloroethane thereto to give a second mixture, and removing an aqueous layer from the second mixture to give a third mixture containing 1,2-benzisoxazole-3-acetic acid and 1,2-dichloroethane;

(c) removing water from the third mixture by distillation to give a fourth mixture, adding chlorosulfonic acid to the fourth mixture and reacting the mixture to give a fifth mixture, and adding a base to the fifth mixture to give a sixth mixture containing an alkali metal salt of 1,2-benzisoxazole-3-methanesulfonic acid;

(d) adding phosphoryl chloride (also known as phosphorous oxychloride) to the sixth mixture, and reacting the mixture to give a seventh mixture containing 1,2-benzisoxazole-3-methanesulfonyl chloride;

(e) adding ammonia to the seventh mixture and reacting the mixture to give an eighth mixture containing 1,2-benzisoxazole-3-methanesulfonamide; and (f) isolating the 1,2-benzisoxazole-3-methanesulfonamide.

The reaction in (a) is preferably conducted in the presence of a chelating agent to give the first mixture.

Preferably the first mixture is washed with 1,2-dichloroethane before acidifying the first mixture in (b).

The present invention also provides a one-pot process for the preparation of 1,2-benzisoxazole-3-methanesulfonamide, which comprises:

(i) reacting 1,2-benzisoxazole-3-acetic acid and chlorosulfonic acid in 1,2-dichloroethane to give a first mixture, and adding a base thereto to give a second mixture containing an alkali metal salt of 1,2-benzisoxazole-3-methanesulfonic acid;

(ii) adding phosphoryl chloride to the second mixture, and reacting the mixture to give a third mixture containing 1,2-benzisoxazole-3-methanesulfonyl chloride;

(iii) adding ammonia to the third mixture and reacting the mixture to give a fourth mixture containing 1,2-benzisoxazole-3-methanesulfonamide; and (iv) isolating the 1,2-benzisoxazole-3-methanesulfonamide, wherein all of (i) to (iii) are conducted in a single reactor without isolating intermediates in solid form.

Furthermore, the present invention provides a process for the preparation of 1,2-benzisoxazole-3-acetic acid, which comprises reacting 4-hydroxycoumarin, hydroxylamine or an acid addition salt thereof, and a base in water, and acidifying the resulting reaction mixture.

In the above process for the preparation of 1,2-benzisoxazole-3-acetic acid, the reaction of 4-hydroxycoumarin, hydroxylamine or an acid addition salt thereof, and a base is preferably conducted in the presence of a chelating agent.

In the preferred embodiment, the above process for the preparation of 1,2-benzisoxazole-3-acetic acid further comprises washing the reaction mixture of 4-hydroxycoumarin, hydroxylamine or an acid addition salt thereof, and a base with 1,2-dichloroethane before acidifying thereof.

In further preferred embodiment, the above process for the preparation of 1,2-benzisoxazole-3-acetic acid comprises reacting 4-hydroxycoumarin, hydroxylamine or an acid addition salt thereof, and a base in water in the presence of a chelating agent and washing the resulting reaction mixture with 1,2-dichloroethane before acidifying thereof.

The process for the preparation of 1,2-benzisoxazole-3-methanesulfonamide of the present invention is a process for the preparation of 1,2-benzisoxazole-3-methanesulfonamide without isolating intermediates in solid form, more particularly, a process for the preparation of 1,2-benzisoxazole-3-methanesulfonamide, which comprises using 4-hydroxycoumarin as a starting compound, and water and 1,2-dichloroethane as a solvent, without isolating intermediates in solid form. Additionally, the process of the invention may be carried out in a single reactor (one-pot). However, in (b) above, an aqueous layer is removed from the second mixture consisting of two layers, i.e. the aqueous layer and a 1,2-dichloroethane layer. In this liquid-liquid extraction by batch method, a lower layer is usually transferred to another vessel. Therefore, a process for the preparation of 1,2-benzisoxazole-3-methanesulfonamide using multiple vessels, preferably two vessels, is also within the scope of the invention.

4-Hydroxycoumarin is commercially available or may be prepared by a conventional method or a modified method thereof.

The "hydroxylamine" may be a commercially available aqueous hydroxylamine solution, but more preferably is prepared by reacting an acid addition salt of hydroxylamine with a base in a reactor.

The "base" includes, for example, sodium hydroxide, potassium hydroxide, sodium carbonate, potassium carbonate, etc. Among them, sodium hydroxide and potassium hydroxide are preferable, and sodium hydroxide is most preferable. Usually, these bases are used in the form of an aqueous solution.

Examples of the "acid addition salt of hydroxylamine" are hydroxylamine hydrochloride, hydroxylamine sulfate, hydroxylamine nitrate, hydroxylamine phosphate, etc., and among them, hydroxylamine sulfate is preferable.

The "chelating agent" includes, for example, ethylenediaminetetraacetic acid, an alkali metal salt of ethylenediaminetetraacetic acid, an ammonium salt of ethylenediaminetetraacetic acid, an alkali metal salt of hydroxyethylethylenediaminetriacetic acid, an alkali metal salt of dihydroxyethylethylenediaminediacetic acid, 1,3-propanediaminetetraacetic acid, diethylenetriaminepentaacetic acid, an alkali metal salt of diethylenetriaminepentaacetic acid, an alkali metal salt of triethylenetetraminehexaacetic acid, an alkali metal salt of hydroxyethyliminodiacetic acid, and hydrates thereof. Preferable chelating agents are ethylenediaminetetraacetic acid, a sodium salt of ethylenediaminetetraacetic acid, a potassium salt of ethylenediaminetetraacetic acid, an ammonium salt of ethylenediaminetetraacetic acid, and hydrates thereof. Among them, a sodium salt of ethylenediaminetetraacetic acid and hydrates thereof are more preferable.

In case that the reaction mixture contains plenty of metal ions (e.g. iron ions), and there is a possibility of a rapid decomposition of hydroxylamine, the reaction temperature can be easily controlled by addition of a chelating agent thereto. The reaction temperature of the present process is usually in the range of 60° C. to 100° C., preferably in the range of 80° C. to 90° C., more preferably in the range of 84° C. to 86° C.

Examples of the "acid" are hydrochloric acid, sulfuric acid, acetic acid, etc., and among them, hydrochloric acid or sulfuric acid is preferable, and sulfuric acid is more preferable.

Since water is contained in the third mixture of 1,2-benzisoxazole-3-acetic acid and 1,2-dichloroethane in (b), the water is removed by distillation from this mixture prior to the reaction with chlorosulfonic acid.

The reaction of 1,2-benzisoxazole-3-acetic acid with chlorosulfonic acid may proceed in the presence or absence of dioxane. The reaction temperature thereof is usually in the range of 60° C. to 80° C.

The "alkali metal salt of 1,2-benzisoxazole-3-methanesulfonic acid" is preferably 1,2-benzisoxazole-3-methanesulfonic acid sodium salt.

In the preparation of an alkali metal salt of 1,2-benzisoxazole-3-methanesulfonic acid, an aqueous solution of a base is usually used therein, and hence, water is removed by distillation from a mixture containing an alkali metal salt of 1,2-benzisoxazole-3-methanesulfonic acid prior to the subsequent reaction with phosphoryl chloride.

In the reaction of an alkali metal salt of 1,2-benzisoxazole-3-methanesulfonic acid with phosphoryl chloride, it is preferable to add a tertiary amine such as triethylamine into the reaction mixture. The reaction temperature is usually in the range of 75° C. to 85° C.

The "ammonia" is preferably ammonia gas, and the reaction temperature is preferably in the range of 30° C. to 60° C.

The isolation step of 1,2-benzisoxazole-3-methanesulfonamide in (f) is carried out by concentrating the reaction mixture, adding water thereto, stirring the mixture, followed by collecting the crystals by filtration. The crystals of 1,2-benzisoxazole-3-methanesulfonamide isolated from the mixed solvent of water and 1,2-dichloroethane are of high purity.

The isolated 1,2-benzisoxazole-3-methanesulfonamide in (f) is further purified by recrystallization to increase the purity thereof. The solvent for recrystallization includes, for example, aqueous ethanol, aqueous isopropanol etc., among them, aqueous isopropanol is preferable, and isopropanol containing water in an amount of 45 to 55% by volume is more preferable. By further carrying out azeotropic distillation of 1,2-dichloroethane in the recrystallization step, there are obtained crystals of 1,2-benzisoxazole-3-methanesulfonamide containing residual 1,2-dichloroethane of not more than 5 ppm.

BEST MODE FOR CARRYING OUT THE INVENTION

The present invention is illustrated in more detail by the following Examples, but the present invention should not be construed to be limited thereto. The purity of the products was measured by high performance liquid chromatography.

EXAMPLE 1

1) A mixture of hydroxylamine sulfate (43 g), water (113 ml) and a 25% aqueous sodium hydroxide solution (57 ml) is stirred, and thereto are added 4-hydroxycoumarin (21 g) and ethylenediaminetetraacetic acid disodium salt dihydrate (0.4 g), and the mixture is stirred with heating at 84° C. to 86° C. for 4 hours. The reaction mixture is cooled, and thereto are added 1,2-dichloroethane (30 ml) and water (43 ml), and the mixture is stirred. The 1,2-dichloroethane layer is removed, and the pH value thereof is adjusted to pH 1-2 with 62.5% sulfuric acid. The mixture is extracted twice with 1,2-dichloroethane (120 ml and 10 ml) to give a mixture of 1,2-benzisoxazole-3-acetic acid and 1,2-dichloroethane. The purity of 1,2-benzisoxazole-3-acetic acid in this mixture is 98%.

2) Water is removed by distillation from the above mixture of 1,2-benzisoxazole-3-acetic acid and 1,2-dichloroethane, and thereto is added dropwise chlorosulfonic acid (15.5 g) while the internal temperature is kept at 63° C.-79° C. After the addition, the mixture is stirred for 90 minutes while the reaction temperature is kept at 63° C.-79° C. After cooling, a 25% aqueous sodium hydroxide solution is added to the reaction mixture so as to adjust the pH value thereof to pH 11 or above. Water is removed by distillation from the reaction mixture to give a mixture of sodium 1,2-benzisoxazole-3-methanesulfonate and 1,2-dichloroethane. Triethylamine (2.4 g) and phosphoryl chloride (17.5 g) are added to this mixture, and the mixture is stirred at a temperature of 77° C.-83° C. for 6 hours. After cooling, to the reaction mixture is added 1,2-dichloroethane (80 ml), and ammonia gas is blown into the mixture until saturated while the reaction temperature is kept at 30° C.-60° C. The reaction mixture is concentrated, and water is added thereto. The mixture is stirred, and the precipitated crystals are collected by filtration, and washed with water to give crude crystals of 1,2-benzisoxazole-3-methanesulfonamide. The purity of the crude crystals is 96%.

3) The above crude crystals are recrystallized from a 50% aqueous isopropanol, and dried at 80° C. for 16 hours to give crystals of 1,2-benzisoxazole-3-methanesulfonamide having a purity of 99%.

EXAMPLE 2

A mixture of hydroxylamine sulfate (344.0 g), water (904 ml) and a 25% aqueous sodium hydroxide solution (456 ml) is stirred, and thereto are added 4-hydroxycoumarin (168.0 g) and ethylenediaminetetraacetic acid disodium salt dihydrate (3.2 g), and the mixture is stirred with heating at 84° C.-86° C. for 4 hours. The reaction mixture is cooled, and thereto is added 1,2-dichloroethane (240 ml). The mixture is stirred, and the aqueous layer is collected. The pH value of the aqueous layer is adjusted to pH 1-2 with 25% sulfuric acid, and the precipitated crystals are collected by filtration, washed with water, and dried with air at 60° C. for 15 hours to give 1,2-benzisoxazole-3-acetic acid (170.4 g).

INDUSTRIAL APPLICABILITY

From the above description, the present invention provides a process for the preparation of 1,2-benzisoxazole-3-methanesulfonamide using 1,2-benzisoxazole-3-acetic acid as a starting compound and 1,2-dichloroethane as a solvent, or 4-hydroxycoumarin as a starting compound and water and 1,2-dichloroethane as solvents, by which 1,2-benzisoxazole-3-methanesulfonamide can be effectively prepared in a one-pot system without isolating intermediates in solid form. Moreover, the present invention also provides an industrially useful process for the preparation of 1,2-benzisoxazole-3-acetic acid, which comprises reacting 4-hydroxycoumarin and hydroxylamine in water in the presence of a chelating agent.

The invention claimed is:

1. A one-pot process for the preparation of 1,2-benzisoxazole-3-methanesulfonamide, which comprises:
   (i) reacting 1,2-benzisoxazole-3-acetic acid and chlorosulfonic acid in 1,2-dichloroethane to give a first mixture, and adding sodium hydroxide thereto to give a second mixture containing sodium 1,2-benzisoxazole-3-methanesulfonate;
   (ii) adding phosphoryl chloride to the second mixture, and reacting the mixture to give a third mixture containing 1,2-benzisoxazole-3-methanesulfonyl chloride;
   (iii) adding ammonia gas to the third mixture and reacting the mixture to give a fourth mixture containing 1,2-benzisoxazole-3-methanesulfonamide; and
   (iv) isolating the 1,2-benzisoxazole-3-methanesulfonamide, wherein all of (i) to (iii) are conducted in a single reactor without isolating intermediates in solid form.

2. The one-pot process according to claim 1, wherein in step (i) is conducted in the presence of dioxane.

3. The one-pot process according to claim 1, wherein in step (i) is conducted in the absence of dioxane.

4. The one-pot process according to claim 1, wherein the reaction of 1,2-benzisoxazole-3-acetic acid with chlorosulfonic acid is conducted at a temperature in the range of 60° C. to 80° C.

5. The one-pot process according to claim 1, wherein a tertiary amine is added to the second reaction mixture in step (ii).

* * * * *